United States Patent
Clark et al.

(10) Patent No.: US 6,280,413 B1
(45) Date of Patent: Aug. 28, 2001

(54) THROMBOLYTIC FILTRATION AND DRUG DELIVERY CATHETER WITH A SELF-EXPANDING PORTION

(75) Inventors: David W. Clark; Souise S. Clark, both of Eden Prairie; Victor I. Chornenky, Minnetonka; Michael R. Forman, St. Paul; Jeffrey A. Lee, Plymouth, all of MN (US)

(73) Assignee: Medtronic Ave, Inc., Santa Rosa, CA (US)

(*) Notice: Subject to any disclaimer, the term of this patent is extended or adjusted under 35 U.S.C. 154(b) by 0 days.

(21) Appl. No.: 08/889,432

(22) Filed: Jul. 8, 1997

Related U.S. Application Data

(63) Continuation of application No. 08/483,201, filed on Jun. 7, 1995, now abandoned.

(51) Int. Cl.[7] .................................................. A61M 29/00
(52) U.S. Cl. ........................... 604/104; 604/49; 604/96; 604/280
(58) Field of Search ............................... 604/104, 95–97, 604/99, 49, 51, 280–282, 264, 27, 28

(56) References Cited

U.S. PATENT DOCUMENTS

| | | | |
|---|---|---|---|
| 3,472,230 | 10/1969 | Fogarty | 128/328 |
| 3,952,747 | 4/1976 | Kimmell, Jr. | 128/303 R |
| 4,430,083 | 2/1984 | Ganz et al. | 604/283 |
| 4,488,877 | 12/1984 | Klein et al. | 604/175 |
| 4,494,531 | 1/1985 | Gianturco . | |

(List continued on next page.)

OTHER PUBLICATIONS

Robert M. Califf, M.D., "Use of a Monoclonal Antibody Directed Against the Platelet Glycoprotein IIb/IIIa Receptor in High–Risk Coronary Angioplasty," *The New England Journal of Medicine*, Apr. 7, 1994, pp. 956–960.

Peter Eichelter, M.D. and Worthington G. Schenk, Jr., M.D., "A New Experimental Approach to Prophylaxis of Pulmonary Embolism," *Forefront: Preliminary Report*, Nov.–Dec. 1967, pp. 455–456.

Peter Eichelter and Worthington G. Schenk, Jr., M.D., "Prophylaxis of Pulmonary Embolism, A New Experimental Approach With Initial Results," *Arch Surg—vol. 97*, Aug. 1968, pp. 348–356.

"Prolyser for Safe Temporary Protection," *Cordis International SA*, Jan. 1995, 3 pages.

"You Can See the Dispatch Difference," *1994 SCIMED Life Systems, Inc.*, 4 pages.

*Primary Examiner*—John D. Yasko

(57) ABSTRACT

A thrombolytic filtration and drug delivery catheter is disclosed comprising a shaft which longitudinal ribs. The ribs are compressed while being advanced to the site of interest and are released at the site, flaring to a diameter greater than the diameter of the shaft. The ribs can be compressed by a sleeve or thread, for example. Drugs or other agents can be delivered through lumens in the shaft and ribs, out through ports in the ribs. Preferably, the ports are positioned to deliver the drugs or other agents between the ribs and within the region defined by the ribs.

35 Claims, 12 Drawing Sheets

U.S. PATENT DOCUMENTS

| | | | |
|---|---|---|---|
| 4,636,195 | 1/1987 | Wolinsky | 604/53 |
| 4,643,184 | 2/1987 | Mobin-Uddin | 128/303 R |
| 4,693,243 | 9/1987 | Buras | 128/207.15 |
| 4,706,671 | 11/1987 | Weinrib | 128/348.1 |
| 4,737,141 | 4/1988 | Spits | 604/28 |
| 4,793,348 | 12/1988 | Palmaz | 128/325 |
| 4,813,925 | 3/1989 | Anderson, Jr. et al. | 604/8 |
| 4,824,436 | 4/1989 | Wolinsky | 604/53 |
| 4,873,978 | 10/1989 | Ginsburg . | |
| 4,874,360 | 10/1989 | Goldberg et al. | 604/8 |
| 4,878,893 | 11/1989 | Chin . | |
| 4,887,996 | 12/1989 | Bengmark | 604/54 |
| 4,950,258 | 8/1990 | Kawai et al. | 604/281 |
| 4,957,470 | 9/1990 | Roemer | 604/8 |
| 4,986,814 | 1/1991 | Burney et al. | 604/164 |
| 4,994,069 | 2/1991 | Ritchart et al. | 606/191 |
| 4,997,435 | 3/1991 | Demeter | 606/127 |
| 5,034,001 | 7/1991 | Garrison et al. | 604/53 |
| 5,062,829 | 11/1991 | Pryor et al. | 604/57 |
| 5,087,244 | 2/1992 | Wolinsky et al. | 604/53 |
| 5,133,733 | 7/1992 | Rasmussen et al. | 606/200 |
| 5,147,379 | 9/1992 | Sabbaghian | 606/206 |
| 5,152,777 | 10/1992 | Goldberg et al. | 606/200 |
| 5,181,911 | 1/1993 | Shturman | 604/96 |
| 5,221,261 | 6/1993 | Termin et al. | 604/104 |
| 5,256,146 | 10/1993 | Ensminger et al. | 604/104 |
| 5,279,565 | 1/1994 | Klein et al. | 604/105 |
| 5,304,120 | 4/1994 | Crandell et al. . | |
| 5,324,304 | 6/1994 | Rasmussen | 606/200 |
| 5,336,178 | 8/1994 | Kaplan et al. | 604/53 |
| 5,342,348 | 8/1994 | Kaplan | 604/891.1 |
| 5,350,398 | 9/1994 | Pavcnik et al. | 606/200 |
| 5,370,657 | 12/1994 | Irie | 606/200 |
| 5,413,586 | 5/1995 | Dibie et al. | 606/200 |
| 5,415,630 | 5/1995 | Gory et al. | 604/53 |
| 5,509,900 | 4/1996 | Kirkman . | |

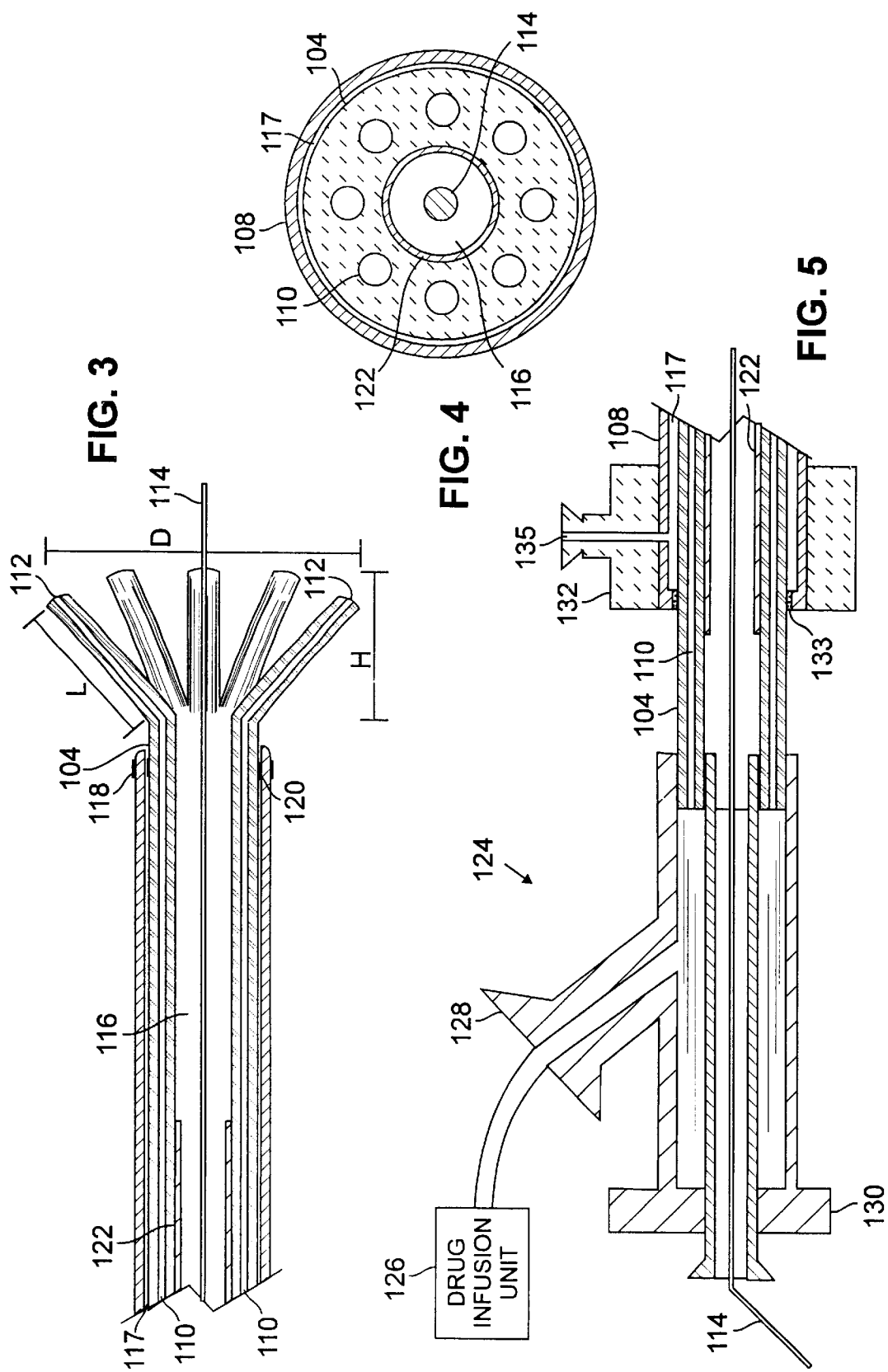

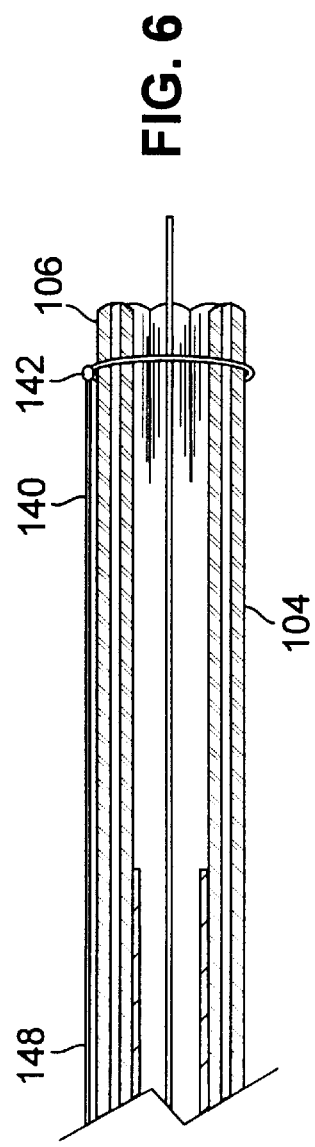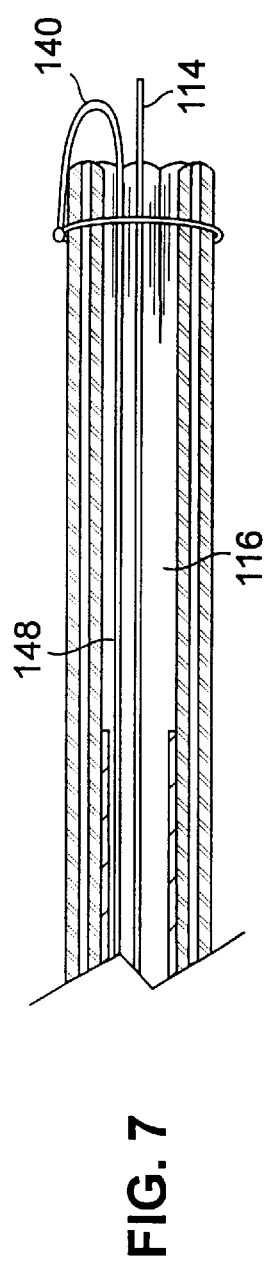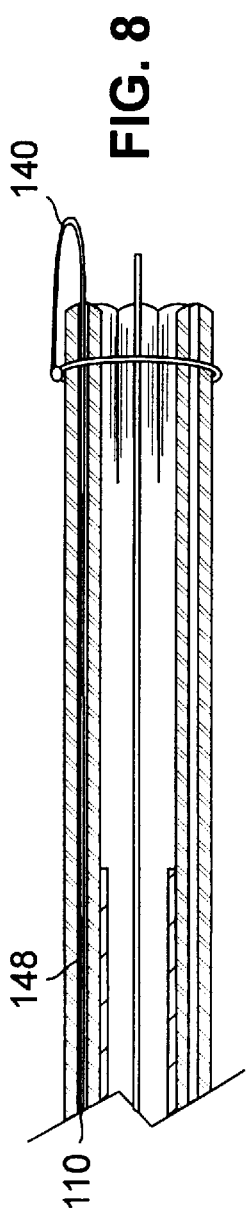

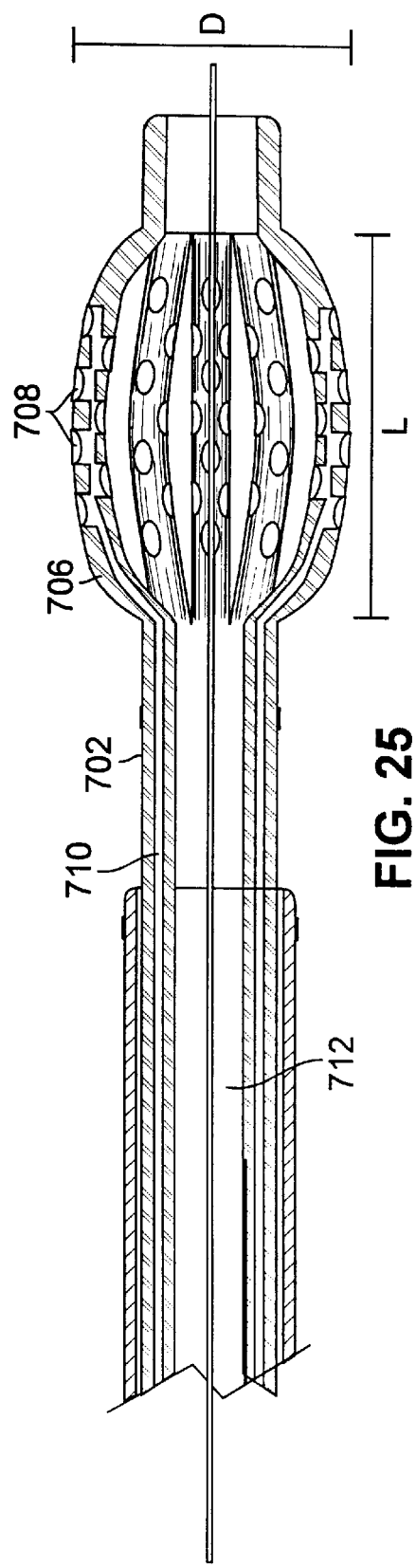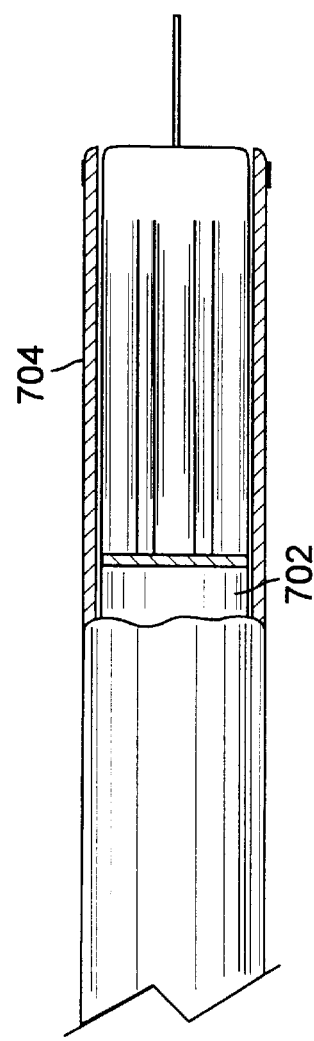

THROMBOLYTIC FILTRATION AND DRUG DELIVERY CATHETER WITH A SELF-EXPANDING PORTION

This is a Continuation of application Ser. No. 08/483,201, filed Jun. 7, 1995 now abandoned.

FIELD OF THE INVENTION

A thrombolytic filtration and drug delivery catheter, and more particularly, a thrombolytic filtration and drug delivery catheter comprising longitudinal ribs which are advanced to the desired site in a compressed position and can be released to a deployed position at the desired site.

BACKGROUND OF THE INVENTION

Catheters serve a variety of functions in medical procedures. In addition to the dilatation of clogged arteries, catheters are used to deliver drugs or other agents to sites in the cardiovascular system, the urethra, bladder, prostate, rectum and central nervous system, such as along the spinal column. Other applications include the delivery and placement of devices, such as a thrombolytic filter.

A variety of thrombolytic filters are available. When positioned, the filters, which are typically in the shape of an umbrella or mesh, expand across the blood vessel. Access to a desired site is often percutaneous, however. The catheter must also often be advanced through narrow vessels or lumens with tortuous turns. A narrow catheter is thus preferred for ease of insertion and advancement. Thrombolytic filters must therefore be capable of being delivered through a narrow catheter shaft.

Such filters typically comprise wires of stainless steel in the desired configuration, compressed for delivery through a catheter. When released from the catheter, they expand across the blood vessel. Shape memory alloys have also been used to form expandable devices which can be delivered in a compressed state and are activated by temperature, for example. The filter can be expanded by a balloon, as well. Some devices include hooks to engage the vessel wall, securing the filter in position. Since thrombosis is most common in the lower extremities, such devices are usually implanted in the inferior vena cava to prevent thrombolytic material from entering the heart, where it could be pumped to the lungs, causing a life threatening pulmonary embolism. Thrombolytic material can also cause a cerebral embolism or myocardial infarction.

Use of metal alloys and wires, however, particularly those with hooks, can damage the tissue of the lumen or vessel, causing thrombosis. The filters may also be difficult to place and remove, particularly when filled with thrombolytic material. Some devices occlude too much of the blood vessel, preventing adequate blood flow. The use of such devices often requires the oral administration of anticoagulants, as well.

A commercially available thrombolytic filtration product, the Prolyser™ from Cordis®, comprises an outer catheter shaft of fluoropolymeric material with longitudinal ribs. An inner catheter shaft runs axially through the outer shaft. The inner shaft is attached to the distal end of the outer shaft, and can be retracted. Retraction of the inner shaft brings the ends of the longitudinal ribs closer together, causing the longitudinal ribs to flare outward toward the walls of a vein. Thrombolytic material flowing through a vein can be caught by and trapped within the flared longitudinal ribs. The inner shaft includes ports for the delivery of lytic agents within the region encompassed by the ribs. The lytic agent may be too dissipated when it reaches the ribs, however, to adequately dissolve thrombolytic material caught between the ribs.

SUMMARY OF THE INVENTION

In accordance with the present invention, a catheter is disclosed which delivers drugs or other agents through a self-expanding filtration portion of the catheter.

In one embodiment of the invention, the catheter comprises a shaft with a proximal and distal portion, the distal portion comprising filtration means which in a first position flares beyond the diameter of the shaft. A means for compressing the filtration means is provided such that when the means for compressing is released from the filtration means, the filtration means flares to its first position. A means for delivering drugs or other agents to the filtration means is also provided. The filtration means is adapted to bear against the walls of a lumen, such as a vein or artery, when released. The filtration means preferably comprises polymeric material.

In accordance with another aspect of the invention, a catheter is disclosed comprising a shaft with a proximal and distal portion, the distal portion comprising a plurality of longitudinal ribs which in a first position flare beyond the diameter of the shaft. The shaft further comprises delivery lumens extending longitudinally through the shaft and ribs and at least one port in each rib for a delivered drug or agent to exit the rib. A sleeve receives at least the distal portion of the shaft. The sleeve and shaft can move with respect to each other such that when the member is retracted from the distal portion, the longitudinal ribs are in their first position and when the distal portion is within the member, the member compresses the ribs into a second position. A plurality of ports are preferably provided around the ribs. The longitudinal ribs are preferably adapted to bear against the walls of a lumen, such as a vein or artery, when released. The longitudinal ribs also preferably comprise polymeric material.

A catheter is also disclosed in accordance with the present invention wherein the longitudinal ribs are compressed by a thread. When the thread is released from the longitudinal ribs, the ribs flare into their first position.

A filtration device is also disclosed in accordance with the present invention, comprising a self-expandable polymeric filter, means for compressing the filter, at least one delivery lumen providing drugs or other agents to the filter and at least one port in the filter in fluid communication with the delivery lumen.

A catheter is also disclosed, wherein the longitudinal ribs are solid.

A method of delivering drugs or other agents within a lumen by a catheter is also disclosed comprising advancing a catheter with compressed, expandable longitudinal ribs to a desired site within the lumen, releasing the compressed longitudinal ribs to allow the longitudinal ribs to flare beyond the diameter of the shaft, and delivering drugs or other agents through the longitudinal ribs. Different drugs or other agents may be delivered through different longitudinal ribs.

A method of filtering thrombolytic material from a vessel within the cardiovascular system is also disclosed comprising advancing a catheter to a desired site within the vessel, and retracting a portion of the catheter to allow a plurality of compressed longitudinal ribs in the distal portion of the catheter to flare beyond the diameter of the catheter to contact the vessel, and delivering a drug or other agent, such as a lytic agent, through the ribs. Different drugs or other agents may be delivered through different longitudinal ribs.

DESCRIPTION OF THE FIGURES

FIG. 3 is a cross-sectional view of the catheter of FIG. 1;

FIG. 4 is a cross-sectional view of the catheter of FIG. 1, through line 4—4 of FIG. 1;

FIG. 5 is a cross-sectional view of the proximal portion of the catheter of FIG. 1;

FIG. 6 is a cross-sectional view of the catheter of FIG. 1, wherein a thread compresses the delivery members;

FIG. 7 is a cross-sectional view of the catheter of FIG. 1, wherein the thread extends through a guide wire lumen;

FIG. 8 is a cross-sectional view of the catheter of FIG. 1, wherein the thread extends through a delivery lumen;

FIG. 25 is a cross-sectional view of the catheter of FIG. 24;

FIG. 26 is a partial cross-sectional view of the catheter of FIG. 24 in its compressed position, wherein the sleeve is partially cut away to reveal the distal portion of the shaft;

DESCRIPTION OF THE INVENTION

The catheter of the present invention, its method of use and its manufacture are shown in FIGS. 24–28. FIGS. 1–23 describe embodiments of catheters which are the subject of another application entitled "Catheters For The Delivery of Drugs And Other Agents Proximate The Walls Of A Lumen Or Vessel, And Methods Of Its Use," application Ser. No. 08/483,201, filed on the same day as the present application and assigned to the assignee of the present application.

Figure 1:
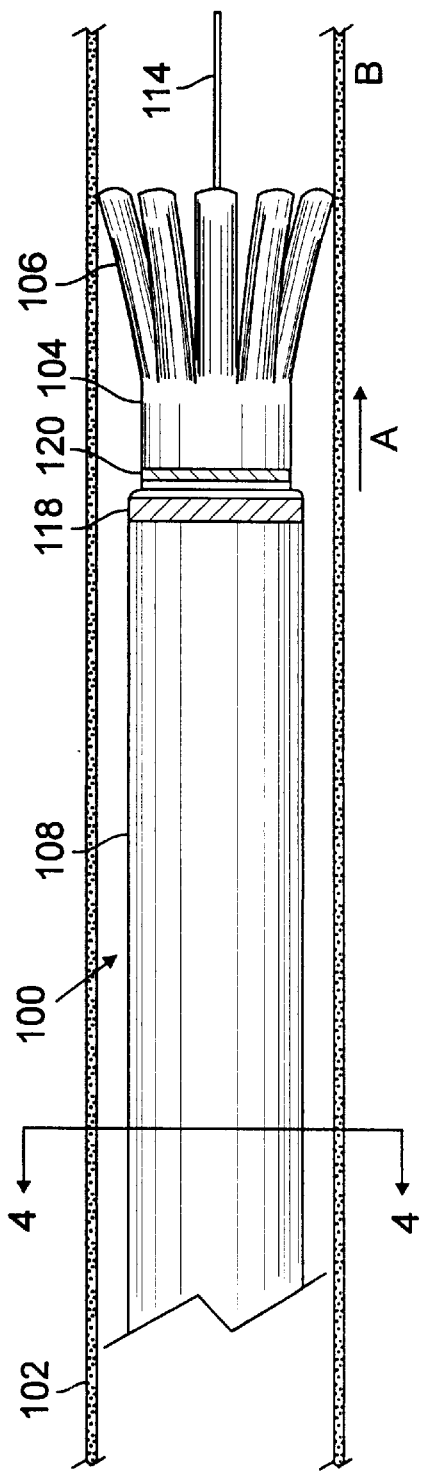
FIG. 1 is a side view of a drug delivery catheter in its deployed position within a lumen, such as an artery.

FIG. 1 is a side view of a catheter 100 deployed to deliver drugs or other agents in a lumen or vessel, such as an artery 102. The catheter comprises a shaft 104 with a distal portion comprising one or more resilient delivery members 106 which flare from the shaft at an acute angle, towards the walls of the artery 102. Eight delivery members 106 are provided in this embodiment, five of which are shown in FIG. 1. The three additional delivery members, obscured in the view of FIG. 1, are shown in FIG. 2.

Figure 2:
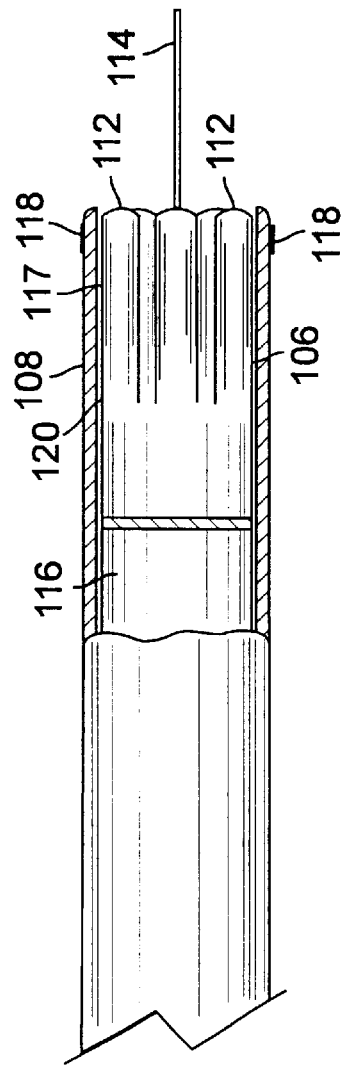
FIG. 2 is a partial cross-sectional view of the catheter of FIG. 1, with a sleeve partially cut away to reveal the distal portion of the shaft, when the catheter is in a non-deployed position.
Figure 9A:
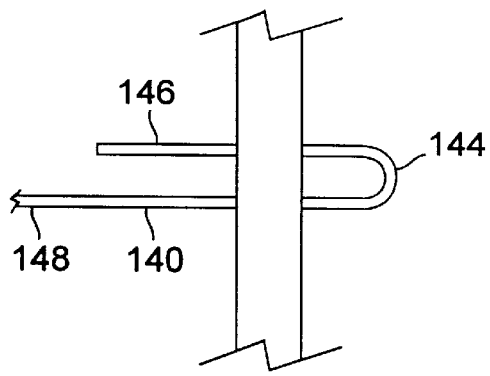
FIGS. 9A–9E illustrate the formation of a releasable knot for use with the embodiments of FIGS. 6–8.
Figure 9B:
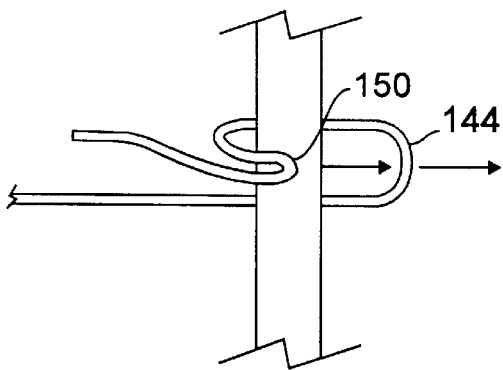
Figure 9C:
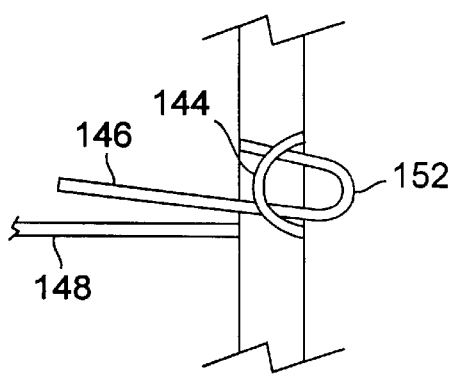
Figure 9D:
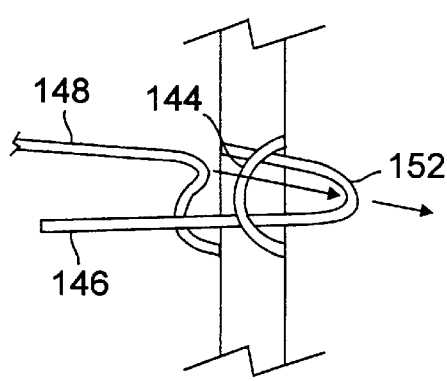
Figure 9E:
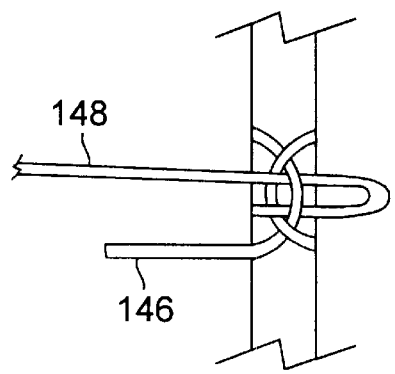

FIG. 2 is a view of the catheter 100 of FIG. 1, in a position prior to deployment. A means is shown in FIG. 2 compressing the resilient delivery members 106. The means is preferably a member, such as a sleeve 108, a portion of which is shown in cross-section in the view of FIG. 2. The sleeve 108 preferably extends over the length of the shaft 104. The sleeve 108 compresses the delivery members 106, maintaining them within the inner diameter of the sleeve 108 while the catheter 100 is stored, advanced to a desired site and, optionally, when the catheter 100 is withdrawn. When the distal end of the catheter 100 is properly positioned at the site of interest B, the delivery members 106 can be released by retracting the sleeve 108, allowing the delivery members 106 of the distal portion to flare outward beyond the outer diameter of the shaft 104 and sleeve 108, to preferably contact and bear against the lumen walls, as in FIG. 1. This ensures that the drug is delivered proximate the wall.

The means for compressing need only extend over the distal portion of the shaft 104 or over the delivery members 106 themselves. A ring, collar, short sleeve or thread can also be used to compress the members. Thread, tubes or rods, for example, can also be coupled to the means for compressing, to withdraw the means for compressing from the delivery members 106. An embodiment using thread to compress and release the delivery members is discussed in conjunction with FIGS. 6–9, below.

Drugs or other agents are delivered through delivery lumens 110 extending longitudinally through the shaft 104 and delivery members 106, as shown in FIG. 3, to ports 112 preferably located at the distal ends of the delivery members 106. The ports 112 deliver the drug proximate the wall of the artery where the fluid flow is very slow. A guide wire 114 and a guide wire lumen 116 extending axially through the shaft 104 are also shown in this view.

Preferably, the drug is delivered upstream of the site with respect to the blood flow so that the slow blood flow proximate the wall atraumatically carries the drug over the site. In FIG. 1, the direction of blood flow is indicated by an arrow A and the site is indicated by B.

FIG. 4 is a cross-sectional view of the catheter of FIG. 1 along line 4—4. The guide wire lumen 116 and the eight drug delivery lumens 110, one for each delivery member 106, are shown. The same drug or agent can be delivered through all eight lumens and members, or different drugs or agents can be delivered through some or all of the lumens and members. While the term "drug" is generally used hereafter, it is understood that other agents can be delivered as well.

The number of delivery members 106 can vary. The preferred number can depend on the diameter of the vessel where the drug is to be delivered. For example, eight delivery members 106 are preferably provided in this embodiment, which will enable an even distribution of the delivered drug around the circumference of the arterial wall in an artery with a diameter of between about 2.5–5 mm. Additional delivery members 106 could be preferred for larger vessels, while fewer can be used in smaller vessels. The delivery members 106 are preferably integral portions of the catheter shaft 104, and are of the same polymeric material as the shaft 104.

As mentioned above, the delivery members 106 preferably bear against the wall of the lumen when fully deployed to ensure drug delivery proximate the walls of the artery. The force with which the members 106 bear against the wall also prevents the members 106 from being displaced from the walls of the artery, or other such lumen, by blood or fluid flow. In coronary arteries, the pumping of the heart could also displace the members. The bearing force is insufficient to damage the walls of the vessel.

To provide such a stabilizing, bearing force, the delivery members 106, when fully extended, preferably have an outermost diameter D, measured across a circumference defined by the outer tips of the members, as shown in FIG. 3, slightly greater than the diameter of the vessel. The delivery members 106 preferably extend from the shaft at an angle of between about 25–50° when fully deployed. The wall of the vessel or lumen preferably compresses the delivery members 10–50% from their fully flared positions. The lesser of 10% or 0.4 mm compression of the diameter is most preferred. Preferably, the ratio between the diameter D when fully flared and the horizontal distance H from the shaft 104 to a projection of the tip of the member to the longitudinal axis, is between about 2:1 to 1:1, to achieve sufficient bearing force against the lumen wall.

For example, the diameters of the arteries can vary between about 2.5–8.0 mm. If the catheter is intended for use in an artery with a diameter of about 3.0 mm, the delivery members are preferably configured to have an outer diameter D of about 3.3 mm when fully extended. If the members 106 flare from the shaft 104 at an angle of about 45°, the length L of the members 106 would be about 2.3 mm. For use in a larger artery, with an inner diameter of about 8 mm, for example, the diameter D between opposing members can be about 8.4 mm. If the members 106 flare from the shaft 104 at an angle of about 45°, the length of each member 106 is about 6 mm.

The inner diameters of the delivery lumens 110 and their ports 112 are preferably between about 0.005–0.010 inches. If greater drug delivery is desired, larger delivery lumens 110 can be provided.

The diameters of the shaft 104 and sleeve 108 may vary dependent upon the diameter of the intended site. For example, in regions of arteries having diameters of between about 2.5–5 mm, the outer diameter of the sleeve 108 can be about 0.065 inches or less. The inner diameter of the sleeve 108 is preferably about 0.055 inches. The outer diameter of the shaft 104 can be about 0.045 inches. Clearance 117 is preferably provided between the sleeve 108 and the shaft 104 to ease the movement of one with respect to the other, as shown in FIGS. 2–4. A larger diameter catheter may be desired for a site with a larger diameter while a smaller diameter catheter may be used for a narrower site. The diameter of the guide wire lumen 116 can be about 0.022 inches, for example.

When flared, the drug delivery members 106 are separated by sufficient space to allow for significant perfusion of blood between the members. This increases the possible length of surgical procedures, without requiring perfusion means which can increase the complexity of the use and manufacture of the catheter.

Returning to FIG. 1, the sleeve 108 preferably includes a radiopaque band 118 of gold or tantalum, for example, at its distal end, to assist in tracking the progress of the catheter on a fluoroscope during a procedure. The shaft 104 also preferably includes a radiopaque band 120, preferably just proximal to the point where the delivery members 106 separate from the shaft 104. The bands 118, 120 are preferably positioned such that when the radiopaque band 118 of the sleeve 108 is essentially aligned with the radiopaque band 120 of the shaft 104, the sleeve 108 has been sufficiently retracted to release the delivery members 106, as shown in FIG. 3. The sleeve 108 may be further retracted from the distal end of the shaft 104 during use, as well.

The sleeve 108 and shaft 104 preferably comprise materials which will easily slide with respect to each other. The shaft 104 is also preferably a thermoplastic elastomer with shape memory capability with proper processing, as described below. The shaft 104 can be a thermoplastic elastomer resin such as a polyether block amide (PEBA). PEBAX®, available from Atochem Inc., New Jersey, is one such material. A hardness of between about 25–50 Shore D is preferred for the shaft 104, with a hardness of 40 most preferred. The characteristics of an appropriate material, PEBAX® grade 4033 SA 00, for example, appear below:

| | |
|---|---|
| Hardness Shore D | 40 |
| Shore A | 90 |
| Melt Flow Rate | 3–7 |
| ASTM D1238 Q | |
| 2 mm orifice | |
| Water Absorption | 1.2% |
| 24 hours | |
| ASTM D 570 | |
| Equilibrium | 0.5% |
| 20° C./65% RH | |
| Elongation | 485% |
| ASTM D638 | |
| At Break | |
| Tensile Strength | 36 MPa |
| ASTM D638 | 5220 psi |
| At Break | |
| Flexural Modulus | 75 MPa |
| ASTM D790 | 10,900 psi |
| Maximum Flexure | 27 mm |
| ASTM D790 | 1.06 inches |
| Stress | 4.3 MPa |
| ASTM D790 | 624 psi |
| Resilience | 62.5% |
| BS 903 Part 08 | |
| Method A | |
| Melting Point (Optical) | 168° C. |
| ASTM D2117 | 334° F. |
| Melting Range DSC | 119–170° C. |
| ASTM D3418 | 246–338° F. |
| Vicat Softening Point | 132° C. |
| ASTM D1525 | 270° F. |

Hytrel®, a polyester elastomer available from Du Pont, Wilmington, Delaware, and all the known grades of polyethylene, such as linear low density polyethylene (LLDPE), low density polyethylene (LDPE), high density polyethylene (HDPE) and ultra high density polyethylene (UHDPE), and other thrombogenic materials which are appropriate for catheter shafts and can exhibit shape memory characteristics, can be used, as well.

An appropriate material for the sleeve 108 is Marlex HHM 4903 HDPE, for example, available from Phillips 66, Pasadena, Tex. Characteristics of Marlex HHM 4903, appear below:

| | |
|---|---|
| Melt Index | 0.30 g/10 min |
| Condition 190/2.16 | |
| D 1238 | |
| Tensile Yield Strength | 3600 psi |

-continued

|  |  |
|---|---|
| 2 in. (50 mm) per min. D 638 Type IV | 25 MPa |
| Ultimate Elongation 2 in. (50 min) per min. D 638 Type IV | >600% |
| Flexural Modulus D 790 | 170 psi 1171 MPa |

Another appropriate material for the sleeve 108 is Hytrel® 5556. It may be desirable when using Hytrel® 5556 to provide a distal portion of the shaft of a softer material, such as Hytrel® 4056, for improved flexibility and to prevent tissue damage. Characteristics of Hytrel® 5556 and 4056 appear below:

|  | 5556 | 4056 |
|---|---|---|
| Hardness D 2240 | 55 Shore D | 40 Shore D |
| Melting Point Peak of Endotherm | 201° C. | 145° C. |
| Melt Complete D 3418 | 220° C. | 170° C. |
| Tensile Strength D 638 | 44 MPa | 30 MPa |
| Ultimate Elongation D638 | 560% | 560% |
| Flexural Modulus D 790 | 207 MPa | 48 MPa |
| Resilience Bashore | 53% | 62% |
| Compression Set 22 hours at 70° C. Constant Load (9.3 MPa) D395A | 4% | 27% |
| Vicat Softening Point D1525 | 180° C. | 112° C. |

Other non-thrombogenic materials can be used as well. For example, the sleeve 108 can comprise PEBAX®, with a hardness of 55, for example, polytetrafluoroethylene (PTFE), polyethylene, fluorinated ethylene propylene (FEP), and all the known grades of polyethylene such as LLDPE, LDPE, HDPE and UHDPE.

To further ease movement of the sleeve 108 with respect to the shaft 104, a lubricous coating of silicone, for example, is provided over the shaft 104. To ease transport through the guide catheter and in the vessel, the lubricous coating is preferably provided over the sleeve 108, as well.

If the preferred materials for the sleeve 108 and shaft 104 are not rigid enough to be easily advanced along the guide wire 114 through a guide catheter, a reinforcing sleeve 122 of stainless steel, titanium, or titanium nickel, for example, may be provided within the guide wire lumen 116, as shown in FIGS. 3–5. The reinforcing sleeve 122 preferably extends from the proximal end of the catheter 100, more than half the length of the catheter 100, up to about 12 inches or about 30 mm from the distal end of the shaft 104. Where the guide wire lumen 116 is about 0.022 inches, the reinforcing sleeve 122 can have an outer diameter of about 0.020 inches and an inner diameter of about 0.016 inches, for example.

Other means of reinforcing the catheter can be used as well. For example, the sleeve 108 can be reinforced instead of the shaft 104. A rigid wire or stylet can also be embedded within the sleeve 108 or shaft 104. Irradiation of the sleeve or shaft with an electron beam to increase the cross-linking and hence the stiffness of the polymeric material, can also be used, as is known in the art. A harder material can also be used for the sleeve 108 or shaft 104 than those preferred above, in which case the distal portion of the sleeve or shaft may need to be "necked down" to decrease its outer diameter, increasing its flexibility.

The catheter 100 can be used to deliver antiproliferatives, anticoagulants, or antiplatelet agents, such as heparin, dexamethasone, and Integralin, to the site of a PTCA, PTA or stent procedure to prevent restenosis, for example. The drug can be delivered before or after the dilatation procedure. It can also be used to deliver lytic agents, such a urokinase, streptokinase or rTPA to the site of a thrombus in an artery or vein. A preferred configuration for use in a vein is shown in FIGS. 16–19, and described further below. Other drugs and agents known or to be developed, could be delivered, as well.

FIG. 5 is a cross-sectional view of the proximal portion of the catheter 100, including a manifold 124 for providing a drug or other agent into the delivery lumens 110. The drug is supplied from a drug infusion unit 126 or a syringe (not shown) through a first port 128. The guide wire 114 can extend through a second port 130. A ring 132 at the proximal end of the catheter 100 is attached to the sleeve 108 to advance or retract the sleeve. The sleeve 108 is retracted by withdrawing the ring 132 a sufficient distance so that the distal portion of the sleeve 108 is no longer compressing or restraining the delivery members 106. Advancing the ring 132 advances the sleeve 108 back over the delivery members 106.

A seal, such as an O-ring 133 of latex or silicone, for example, is provided between the ring and proximal portion of the catheter shaft 104 to prevent leakage. A port 135 can be provided through the ring 132 to enable venting of air. Saline may also be delivered through the port 135 to maintain the clearance 117 open. The port 135 could also be used to delivery a drug or other agent, such as heparin, into the vessel. The manifold 124 can be easily modified to deliver different drugs or other agents through different ports, as well.

In use, the catheter 100 can be advanced to the site of interest B over the guide wire 114 through a guide catheter (not shown). The delivery members 106 are preferably positioned such that the drug will be delivered upstream of the site of interest with respect to the blood flow. For example, if the catheter 100 is advanced along the direction of blood flow, the drug delivery would preferably be proximal to the site B, as in FIG. 1. If the catheter 100 is advanced in a direction opposing the blood flow, the drug delivery would preferably be distal to the site, as in the embodiment of FIG. 16.

The sleeve 108 is then retracted by withdrawing the ring 132 a sufficient distance. Preferably, this can be observed by the alignment of the radiopaque bands 118, 120 on the shaft 108 and sleeve 104, as shown in FIG. 3. The delivery members 106 would then rotate through an acute angle, to the position of FIG. 1. The drug or other agent is then delivered proximate the vessel wall. The slow blood flow proximate the vessel wall will atraumatically carry the delivered drug over the site B. Perfusion of blood is not impeded, as blood or other fluids will flow between the delivery members. If desired or necessary, the sleeve 108 can be retracted further than shown in FIG. 1.

When sufficient drug has been delivered, the sleeve 108 can be advanced back over the distal portion of the shaft 104 or the shaft 104 can be withdrawn into the sleeve 108. The catheter 100 can then be removed through the guide catheter. It is also possible to remove this embodiment of the invention through the guide catheter while it is in the deployed position. In addition to delivering drugs through the members, the guide wire 114 can be removed and drugs can be delivered through the guide wire lumen 116. This could be particularly useful in the treatment of thrombosis, where the drug can be directed toward the center of the thrombus, as well as its periphery along the wall of the vessel. In addition, while the drug is preferably delivered proximate the wall of the vessel or lumen, drug can be delivered at various locations across the cross-section of the vessel by varying the degree to which the sleeve is retracted. Drugs can also be delivered through port 135, of FIG. 5, through the clearance 117 between the sleeve 108 and shaft 104.

FIGS. 6–9 show a variation in the embodiment of FIGS. 1–4, wherein instead of a sleeve 108, a thread 140 restrains and compresses the delivery members 106. The thread 140 can be tied around the periphery of the delivery members 106, in a releasable knot 142, such as a horse thief's knot, shown in FIG. 9E. Formation of a horse thief's knot is shown in FIGS. 9A–9D. First, a loop 144 is formed at one end of the thread 140, beneath the delivery members 106. For illustrative purposes, the delivery members are not shown in these views. The loop 144 has a short end 146 and a long end 148. A portion 150 of the short end 146 is carried over the members and beneath the loop 144 as shown in FIG. 9B, to form a second loop 152, as shown in FIG. 9C. The long end 148 is then carried under the short end 146, over the first loop 144 and through the second loop 152. The short end 146 is pulled to tighten the knot. Pulling the long end 148 releases the knot, allowing the delivery members 106 to flare to their deployed position.

The long end 148 of the thread 140 can extend over the exterior of the shaft 104 as shown in FIG. 6, through a lumen within the shaft 104, such as the guide wire lumen 116, as shown in FIG. 7 or through a delivery lumen 110 as shown in FIG. 8. The guide wire lumen 116 can be divided into two lumens, one for the guide wire 144 and one for the thread 140. The thread 140 can be nylon, for example. The thread can have a diameter between about 0.005–0.008 inches, for example. The use of a thread 140 instead of a sleeve decreases the outer diameter of the catheter and may therefore be particularly suited for use in small vessels, such as cerebral arteries which can have diameters of about 1.0–2.5 mm, for example. The proximal portion of the catheter shown in FIG. 5 can be suitably modified for use with this embodiment. For example, no ring 132 is required to retract a sleeve.

Figure 10:
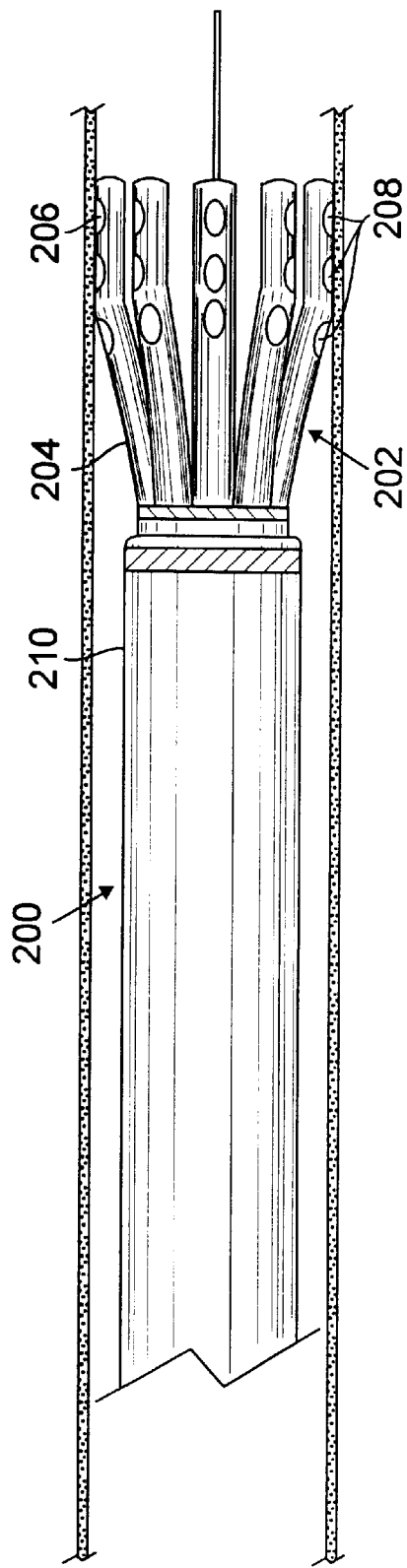
FIG. 10 is a side view of another catheter in its deployed position within a lumen.

FIG. 10 shows another catheter 200 wherein the delivery members 202 comprise a first, tapered portion 204 and a second, longitudinal portion 206. A series of ports 208 can be provided along the tapered and longitudinal portions for delivering drug proximal to the site of interest. A single port can be provided at the distal end of the member, as in the embodiment of FIG. 2, as well. The drug can also be delivered directly onto the site of interest. The ports 208 can have a diameter of about 0.005–0.010 inches. The remainder of the catheter 200 is the same as above.

Figure 11:
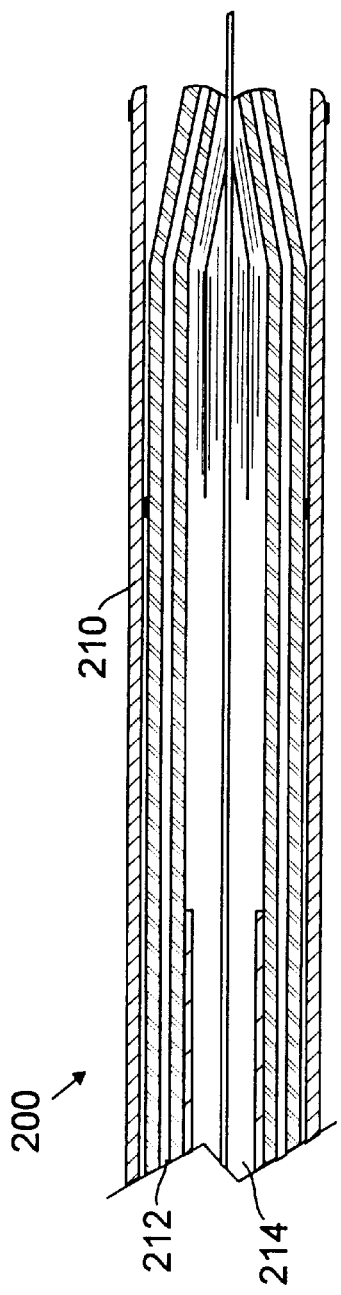
FIG. 11 is a cross-sectional view of the catheter of FIG. 10.

FIG. 11 is a partial cross-sectional view of the catheter 200 wherein the delivery members 202 are within and compressed by a sleeve 210. The sleeve 210 is shown in partial cross-section in this view. Delivery lumens 212 and guide wire lumen 214 are shown as well. The delivery members 202 can be compressed by a thread, as in FIGS. 7–9, or other compressing means, as well. The proximal portion of the catheter 200 can be the same as that shown in FIG. 5.

To manufacture the catheters of the embodiments of FIGS. 1–9, the shaft 104 can be extruded in a multi-lumen extrusion process, as is known in the art. One or both ends of the extrusion can have a tapered portion leading to a wider longitudinal region, to ease subsequent operations on the shaft. Such wider regions can be formed by a bump extrusion process, also known in the art.

The delivery members 106 are formed by cutting the distal end of the shaft 104 between each of the delivery lumens 110 a desired length depending on the desired length for the members. A blade or other thin cutting surface is preferred. The shaft can be cut by hand or by a machine. The machine can include a mounting for securing the shaft and a series of cutting blades disposed radially to simultaneously cut the distal portion of the shaft along its longitudinal axis. The number of blades corresponds to the number of delivery members desired. The thickness of the blades is preferably less than 0.010 inches. A thickness of about 0.005 inches or less is most preferred. If a bump extrusion is used to form the distal end, the distal end is cut through the taper to shorten that end, before cutting the shaft. The shaft can be cut with a laser, as well.

As mentioned above, the length of the delivery members 106 can vary depending on the application. The length of all the delivery members is preferably the same, which enhances the ability of the members to deploy after retraction of the sleeve.

Figure 12:
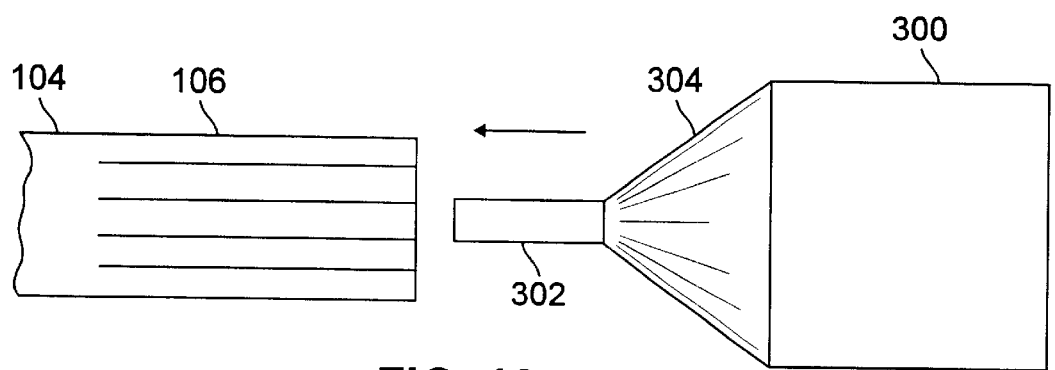
FIGS. 12–13 illustrate steps in the manufacture of the catheters of FIGS. 1 and 10.
Figure 13:
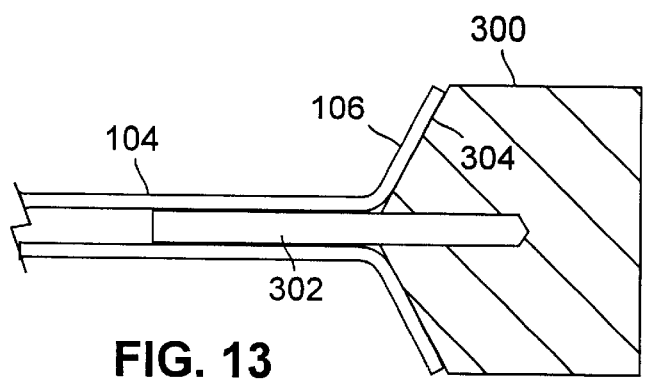

To form the flare in the embodiment of FIGS. 1–6, a tool, such as the tool 300 shown in FIG. 12, is inserted within the guide wire lumen 114 of the extruded shaft 104, after the distal portion is cut, as shown in FIG. 12. The tool 300 comprises a rod shaped guiding mandrel or wire 302 depending from a conical surface 304. As the distal ends of the delivery members 106 engage the conical surface, they are forced outward, as shown in the cross-sectional view of FIG. 13. The tool 300 is advanced to the uncut portion of the shaft. When the tool 300 is suitably positioned, the shaft 104 and tool 300 are placed in an oven at about 225°–250° F. for about 5–30 minutes, to heat set the delivery members 106. In this embodiment, the angle of the flare is preferably between about 25°–50°. If the bump extrusion process is used for the distal end, the delivery members 106 will already be partially tapered. The extent of additional flaring after cutting may not then be as great. The tool 300 can be made of brass, stainless steel or PTFE, for example.

After heat setting, the reinforcing sleeve 122 is inserted into the shaft 104. Radiopaque bands 118, 120 are preferably applied to the shaft 104 and sleeve 108. A lubricous coating is applied to the shaft 104 and the sleeve 108 is placed over the shaft 104 or the thread 140 is tied to the delivery members 106.

Figure 14:
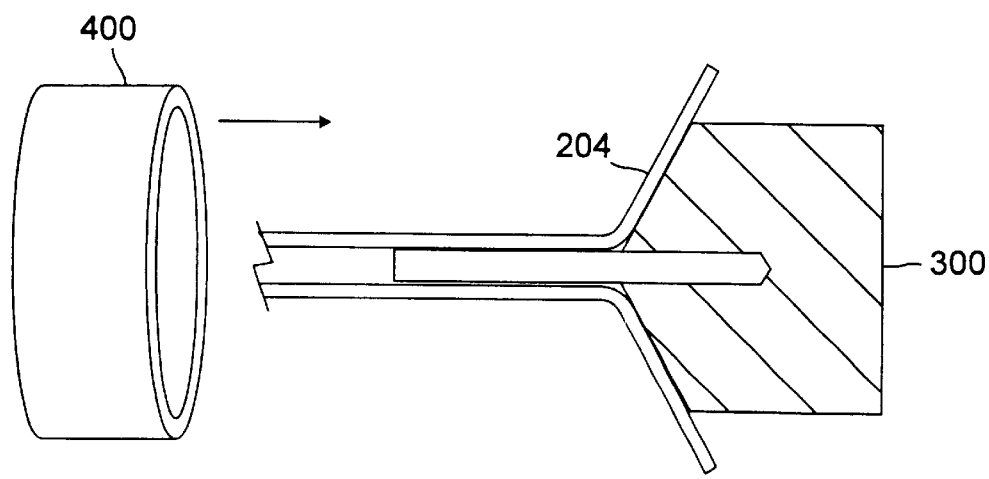
FIGS. 14–15 illustrate further steps in the manufacture of the catheter of FIG. 10.
Figure 15:
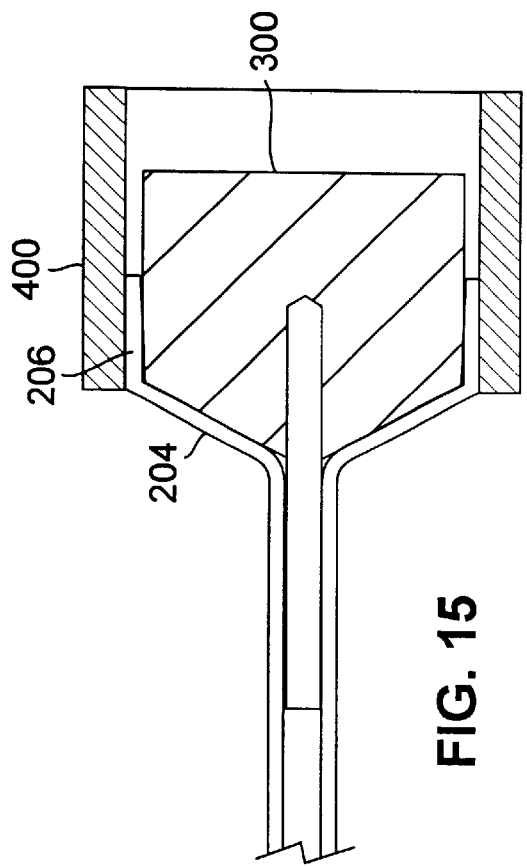

In manufacturing the embodiment of FIGS. 10–11, wherein the delivery members 202 include the second, longitudinal portion 206, the distal end of the shaft is preferably not bump extruded. The first, flared portion of the delivery members 106 can be formed with the same tool as used in the first embodiment. The tool 300 is advanced until the members 202 extend beyond the conical portion of the tool the desired length of the first longitudinal portion 206, as shown in FIG. 14. A tube or collar 400 with a diameter slightly greater than the diameter of the tool 300, is then passed over the proximal end of the shaft, and over the first tool 300, ensuring that the delivery members 202 bear against the wall of the first tool 300, as in the cross-sectional view of FIG. 18. The shaft is then heated, as above. The ports can be formed by a punch, drill or laser, as is known in the art.

FIGS. 16–19 show another catheter, particularly suited for use in a vein, such as the inferior vena cava, or in cerebral arteries. The catheter 500 is the same as the catheter 100 in FIGS. 1–6, except that the delivery members 502 extend rearwardly from the distal end of the shaft 504, as shown in the side view of FIG. 16. The delivery ports 506 are preferably located at the end of the delivery members 502. A plurality of ports can be provided along the inside surfaces of the delivery members 502, as well. This configuration is preferred for delivering drugs or other agents in a vein because in such applications, the catheter is typically inserted into the jugular or femoral vein, in a direction opposite the blood flow, indicated by arrow C in FIG. 16. This configuration delivers the drug or other agent proximate the vessel wall, in the direction of the blood flow. The blood then slowly carries the delivered drug atraumatically across the intended site, indicated by E. Delivery in a direction opposite the blood flow could cause eddy currents, preventing laminar flow along the vessel wall.

Figure 16:
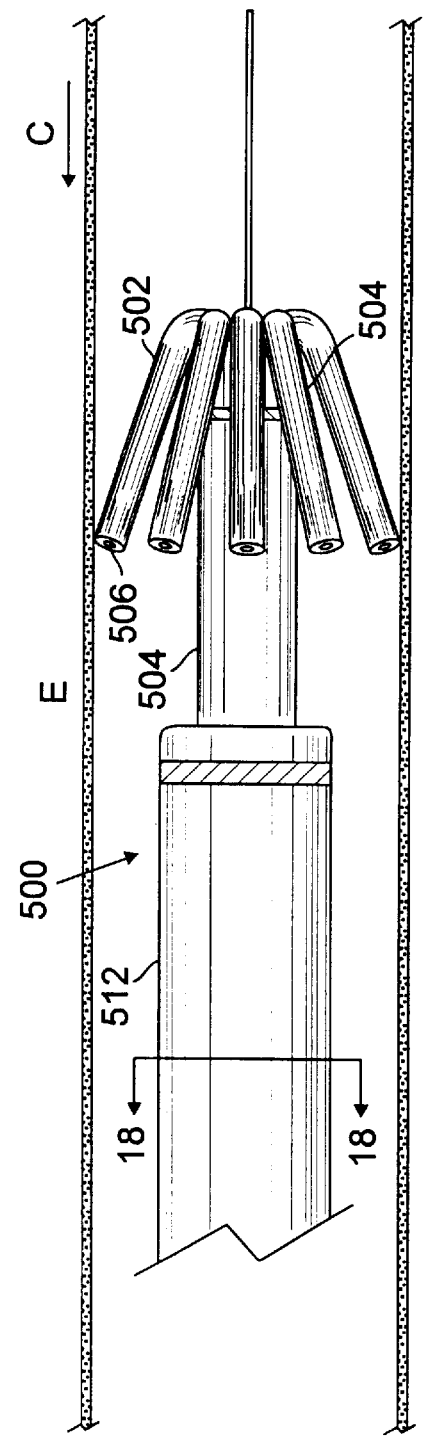
FIG. 16 is a side view of another embodiment of the present invention, deployed within a vein, for example.
Figure 17:
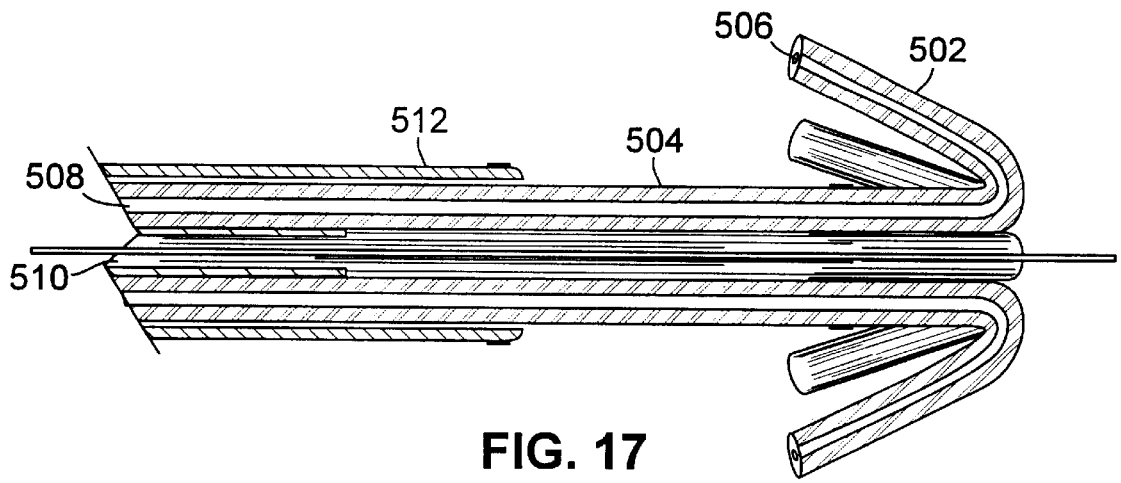
FIG. 17 is a cross-sectional view of the catheter of FIG. 16.
Figure 18:
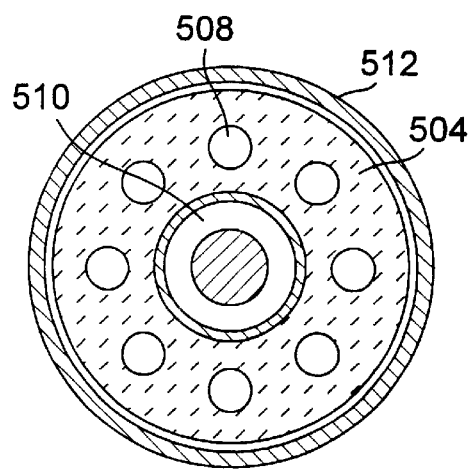
FIG. 18 is a cross-sectional view of the catheter of FIG. 16, through line 18—18.
Figure 19:
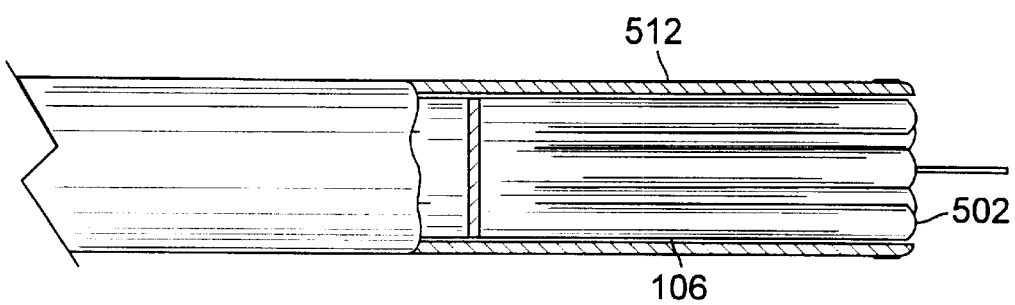
FIG. 19 is a partial cross-sectional view of the catheter of FIG. 16, with a portion of the sleeve in cross-section to reveal the distal portion of the shaft.
Figure 20:
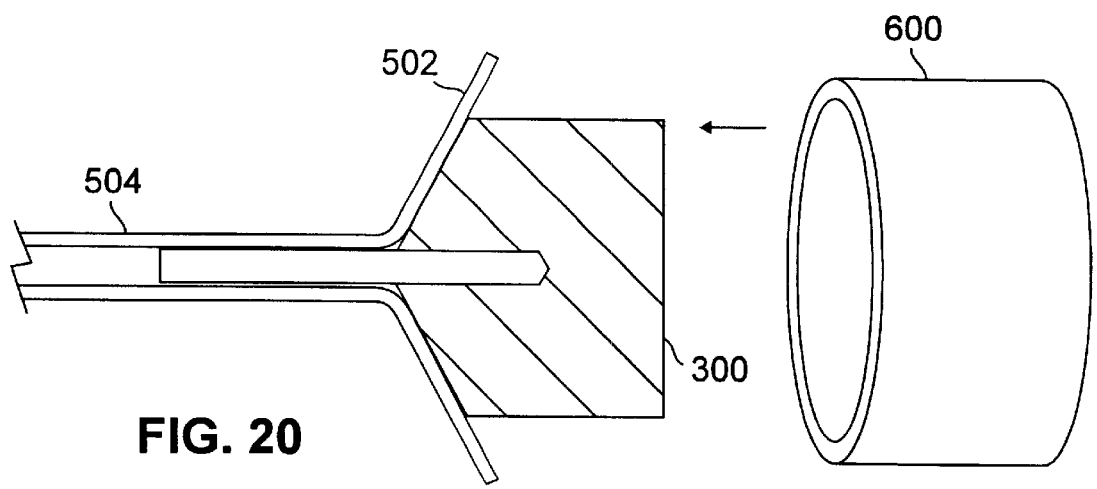
FIGS. 20–23 illustrate steps in the manufacture of the catheter of FIG. 16.

FIG. 17 is a cross-sectional view of the catheter 500 of FIG. 16, showing the delivery lumens 508 and guide wire lumen 510. FIG. 18 is a cross-sectional view of the catheter 500 through line 18—18 in FIG. 16. FIG. 19 is a cross-sectional view of the catheter 500 wherein the delivery members 502 are received within and compressed by the sleeve 512. The proximal portion of the catheter 500 can be the same as that shown in FIG. 5.

As above, the dimensions of the catheter 500 depend on the intended site. For example, the cerebral arteries have a diameter of about 1.0–2.5 mm. Veins, on the other hand, can have diameters of about 6–10 mm. The members 502 preferably have a diameter when fully flared slightly greater than the diameter of the vessel itself, to ensure that they bear against the walls of the vessel. The delivery members 502 preferably rotate through an angle between 115°–140° to reach the position of FIG. 16.

To treat thrombosis, for example, the catheter 500 can be inserted through a guide catheter and over a guide wire, through the thrombus. When the distal portion of the catheter is positioned sufficiently beyond the distal portion of the thrombus, the sleeve 512 can be retracted, releasing the delivery members 502 which rotate through an obtuse angle to the position of FIG. 18. The catheter 500 may need to be advanced slightly to enable the delivery members 502, whose diameter is slightly larger than that of the vessel, to fully rotate. A lytic agent, such as urokinase, streptokinase or rTPA, is then delivered. Integralin may be delivered, as well. Any other drug or agent known or to be developed which is efficacious in dissolving a thrombus, may also be used. Blood flow and the pressure of delivery carry the delivered drug towards the thrombus. The drug is administered until the thrombus is dissolved. When the thrombus is dissolved, the sleeve can be advanced over the distal portion of the catheter prior to its withdrawal.

This configuration can also be used as a filter to catch and remove a thrombus or plaque. The members 502 can be solid, or can include lumens and a series of ports along its surfaces for drug delivery, to dissolve material caught by the members 502. The catheter 500 can be inserted through and beyond a thrombus, and deployed. The distal portion of the catheter can then be withdrawn into the guide catheter, which would be positioned proximal to the thrombus, together with the thrombus.

Alternatively, the catheter can be deployed in a location within a vein or artery to catch thrombolytic material which may pass. A lytic agent, such as those discussed above, can be delivered prior to and during removal of the thrombolytic material by the members. A plurality of ports to allow the delivery of drug along the inside surface of the delivery member can be provided to enable the delivery of a lytic agent directly onto thrombolytic material caught by the members 502. This embodiment could be particularly useful in cerebral arteries.

It may also be advantageous to use the embodiment of FIGS. 1–4 and 16–19 together to apply lytic agent to the proximal and distal sides of the thrombus. First, the catheter 100 can be deployed proximal to the thrombus. Then the catheter 500 can be advanced through and distal to the thrombus over the same guide wire 114 as the catheter 100, and through the guide wire lumen 116 of the catheter 100. Alternatively, the catheter 500 could be deployed first distal to the thrombus and the catheter 100 can then be advanced over it. Lytic agent can then be simultaneously or sequentially supplied through both catheters.

Figure 21:
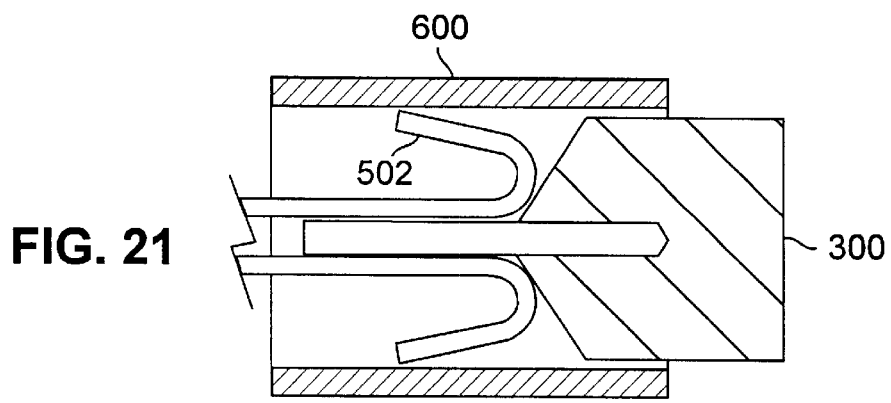
Figure 22A:
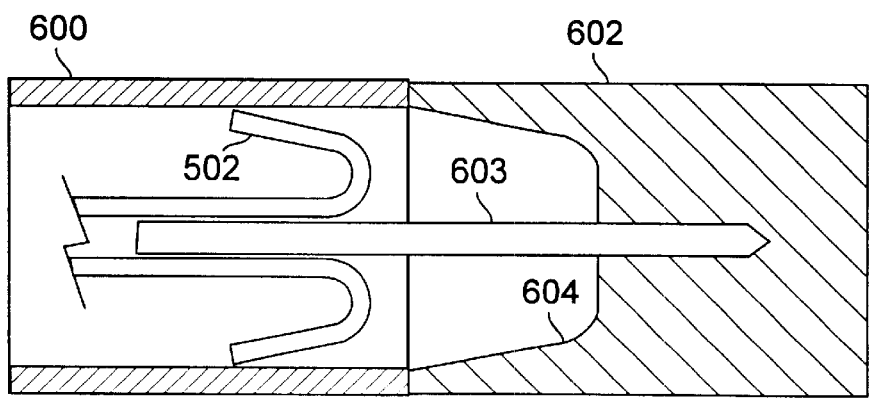
Figure 23:
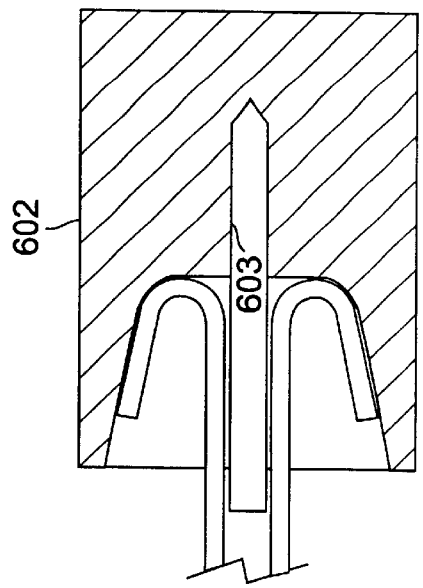
Figure 22B:
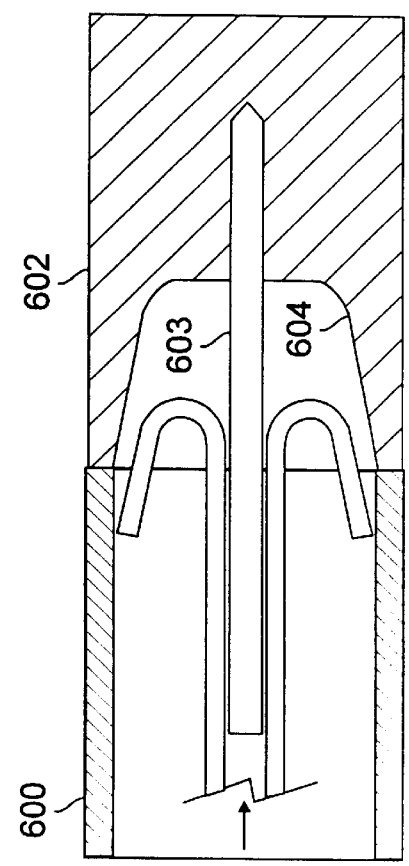

FIGS. 20–23 illustrate the formation of the catheter 500. After cutting the distal portion of the shaft 504, the tool 300 of FIG. 12 is used to flare the members 502. When the members extend past the side walls of the tool 300, as in FIG. 20, a tube or collar 600 is advanced over the distal end of the tool, engaging and forcing the portions of the delivery members backward, as shown in FIG. 21. The first tool is then removed and a second tool 602, shown in cross-section in FIG. 22, is attached to the collar 600. A wire or mandrel 603 depends from the tool 602 and is inserted into the shaft as shown. The second tool 602 is configured to match the desired position of the members 502 when fully deployed. The shaft is advanced in the direction of the arrow from the collar 600 into the second tool 602, over the wire 603. When the shaft 104 is completely within the second tool 602, the delivery members 502 conform to the curvature of the surfaces 604 of the second tool 602, as shown in FIG. 23. The collar 600 is then removed.

The catheter shaft with the tool 602 in place is heated at about 225–250° F. for 5–30 minutes. The catheter shaft is then prepared as above.

Figure 24:
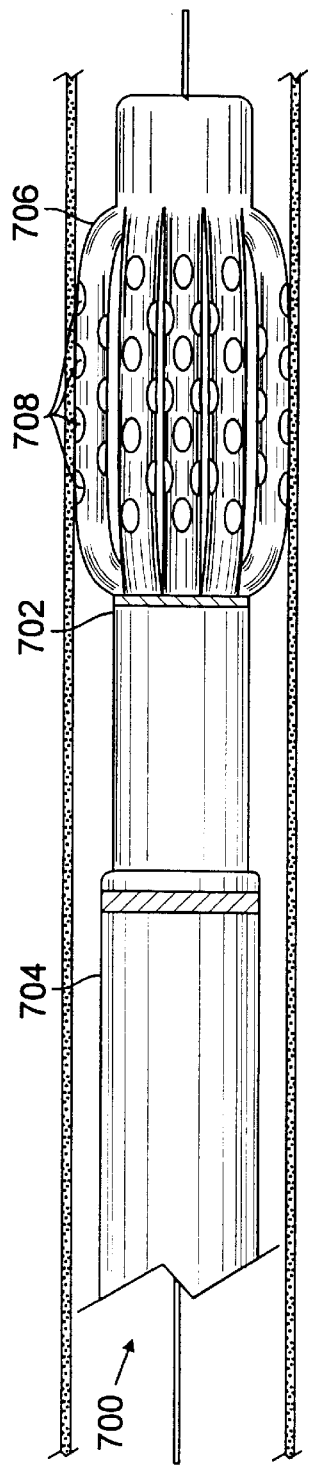
FIG. 24 is a side view of a catheter in accordance with the present invention in its deployed position within a lumen such as the vena cava.

FIGS. 24–26 illustrate a catheter 700 with an expandable distal portion which can be used for drug delivery, as a thrombolytic filter with clot lysing capability, or merely as a thrombolytic filter, in accordance with the present invention. FIG. 24 is a side view of the catheter 700 in its deployed position in the vena cava, for example. The catheter 700 comprises a shaft 702 with an expandable distal portion and a means for compressing the expandable portion, preferably a sleeve 704. Other means for compressing, as described above, may be used as well. The distal portion preferably comprises a plurality of longitudinal ribs 706 having proximal and distal ends depending from the shaft 702. Other configurations, such as overlapping ribs, can also be used. A central portion of the ribs 706 flare radially beyond the outer diameter of the catheter shaft, between the proximal and distal ends of the ribs 706. A portion of the ribs 706 preferably bear against the wall of the vena cava, as shown in FIG. 24. As above, the diameter D of the ribs 706 in their fully flared position, measured across the center of the outer periphery of a region defined by the ribs 706 as shown in FIG. 25, is preferably greater than the diameter of the site, ensuring that the ribs bear against the wall of the lumen.

The longitudinal ribs 706 can be of any desired length, and preferably vary between 6–10 mm. The greatest diameter D of the longitudinal ribs 706 when fully flared is preferably 1.5–2 times their length L, as shown in FIG. 25.

Eight ribs 706 are provided in this embodiment, but more or less can be used, depending on the size of the lumen or vessel at the site of interest.

At least one and preferably a series of ports 708 are provided in each rib 706. Delivery lumens 710 provide drugs or other agents to the ports 708, as shown in FIG. 25. A guide wire lumen 712 is provided, as well. If only to be used for drug delivery to the walls of the vessel, such as to prevent restenosis, the ports 708 preferably extend outward. If the catheter is to be used as a thrombolytic filter, additional ports are preferably provided at the sides of the ribs, for drug delivery between the ribs, and along the underside of the ribs, for drug delivery to the region within the ribs. The ports 708 are preferably about 0.005 inches, and can be formed by a punch, drill or laser. Slits, which can be made by a blade or laser, can be used for drug delivery, as well. A lytic agent, such as those discussed above, or any other useful drug or agent known or to be discovered, can be delivered to dissolve thrombolytic material caught by the filter. The proximal portion of the catheter can be the same as that shown in FIG. 5. The remainder of catheter 700 can be the same as the embodiments above.

FIG. 26 is a partial sectional view of the catheter 700 of FIG. 24, wherein the distal portion of the shaft 702 is completely within the sleeve 704. The sleeve 704 compresses the distal portion of the shaft 702 so that its diameter is less than that of the sleeve 704. The catheter 700 is stored, advanced to the desired site, and preferably withdrawn in this configuration.

The catheter 700 can be advanced to its desired site through a guide catheter, for example, in the configuration of FIG. 26. When the site is reached, the sleeve 704 is retracted, releasing the distal portion of the shaft 702, allowing the longitudinal ribs 706 to flare outward as shown in FIG. 24. Blood or other fluids can flow through the region defined by the ribs 706. Thrombolytic material greater than the distance between the ribs will be caught by the ribs. When the filter is to be removed, the sleeve 704 is advanced or the shaft 702 is retracted such that the distal portion of the shaft is within the sleeve.

If only filtration is desired, the ribs can be solid. No delivery lumens would then be required, either.

Figure 27:
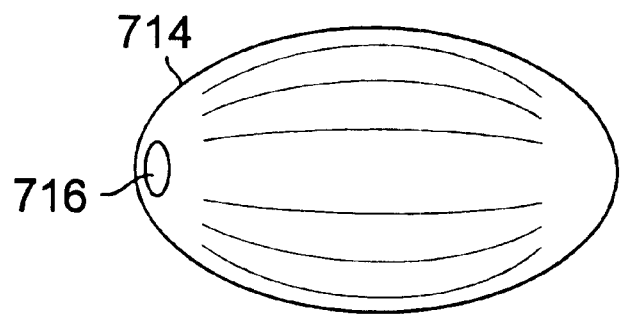
FIG. 27 is a side view of a tool used in the manufacture of the catheter of FIG. 25.
Figure 28:
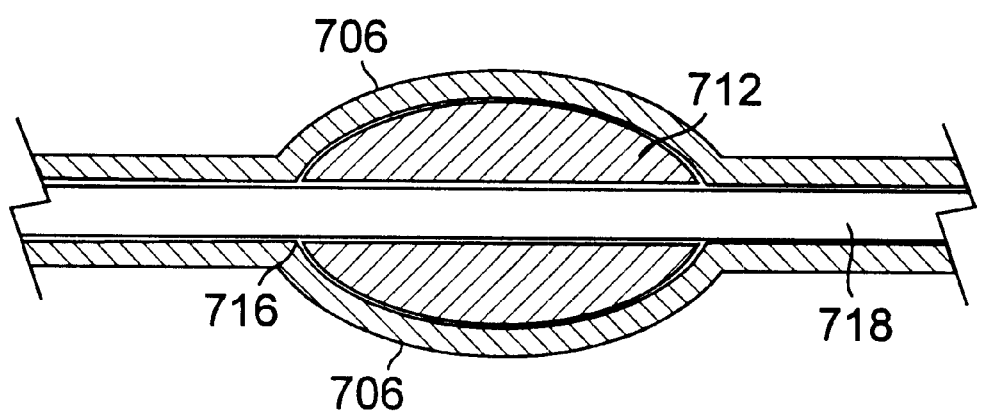
FIG. 28 is a cross-sectional view of the tool of FIG. 27, in position during the manufacture of the catheter of FIG. 25.

The catheter 700 of the present invention can be manufactured of the same materials as described above. The shaft 702 is first extruded, including the delivery lumens 710 if necessary. A wire is then inserted through the distal portion of the guide wire lumen 712. A series of radial longitudinal cuts which do not extend to the distal end of the shaft, are then made with a cutting blade or razor through the shaft, to the guide wire lumen 712, to define the longitudinal ribs 706. The wire is removed and an oblong shaped tool 714, made of brass, stainless steel or PTFE, for example, is then inserted between the ribs. A perspective view of the tool 714 is shown in FIG. 27. A cross-sectional view of the tool 712 and two ribs 706 is shown in FIG. 28. The tool preferably includes an opening 716 along its longitudinal axis for receiving a wire 718 inserted through the distal end of the shaft 702. The wire 718 helps to maintain the tool 714 centered between the ribs 706. The shaft 702 and tool 714 are then heated in an oven, as above. Subsequent processing is the same as above, as well.

The above embodiments are examples of implementations of the present invention, which is defined in the following claims.

We claim:

1. A catheter comprising:
   a shaft with a proximal and distal portion, the distal portion comprising longitudinal ribs which in a first position flare beyond the diameter of the shaft;
   means for compressing the longitudinal ribs such that when the means for compressing is released from the longitudinal ribs, the longitudinal ribs flare to the first position; and
   delivery conduits extending longitudinally through the shaft and ribs and at least one port in each rib for a delivered drug or agent to exit each rib.

2. The catheter of claim 1, wherein the ports are located on an outer periphery of each rib.

3. The catheter of claim 1, wherein the ports are located on sides of each rib.

4. The catheter of claim 1, wherein the ports are located on an underside of each rib.

5. A catheter comprising:
   a shaft with a proximal and distal portion, the distal portion comprising a plurality of longitudinal ribs which in a first position flare beyond the diameter of the shaft, the shaft further comprising delivery lumens extending longitudinally through the shaft and ribs and at least one port in each rib for a delivered drug or agent to exit each rib; and
   a sleeve receiving at least the distal portion of the shaft, wherein the sleeve and shaft can move with respect to each other such that when the sleeve is retracted from the distal portion, the longitudinal ribs are in their first position and when the distal portion is within the sleeve, the member compresses the ribs into a second position.

6. The catheter of claim 5, wherein the ports are located on an outer periphery of each rib.

7. The catheter of claim 5, wherein the ports are located on sides of each rib.

8. The catheter of claim 5, wherein the ports are located on an underside of each rib.

9. The catheter of claim 5, further comprising a plurality of ports located on the outer periphery, sides and underside of each rib.

10. The catheter of claim 5, wherein the shaft further comprises a guide wire lumen.

11. The catheter of claim 5, wherein the ribs are adapted to bear against a lumen wall when released within a lumen.

12. A catheter comprising:
    a shaft with a proximal and distal portion, the distal portion comprising a plurality of longitudinal ribs which in a first position flare beyond the diameter of the shaft, the shaft further comprising delivery conduits extending longitudinally through the shaft and ribs and at least one port in each rib for a delivered drug or agent to exit each rib; and
    thread tied about the longitudinal ribs to compress the ribs in a second position such that when the thread is released from the distal portion, the longitudinal ribs flare into their first position.

13. The catheter of claim 12, wherein the ports are located on an outer periphery of each rib.

14. The catheter of claim 12, wherein the ports are located on sides of each rib.

15. The catheter of claim 12, wherein the ports are located on an underside of each rib.

16. The catheter of claim 12, further comprising a plurality of ports on the outer periphery, sides and undersides of each rib.

17. The catheter of claim 12, further comprising a guide wire lumen.

18. The catheter of claim 12, wherein the ribs are adapted to bear against a lumen wall when released within a lumen.

19. A method of delivering drugs or other agents within a lumen by a catheter comprising:

advancing the catheter with compressed, expandable-hollow, longitudinal ribs to a desired site within the lumen;

releasing the compressed longitudinal ribs, to allow the expandable longitudinal ribs to flare beyond the diameter of the shaft; and delivering drugs or other agents to the site through the longitudinal ribs.

20. The method of claim 19, wherein the ribs bear against the walls of the lumen when flared.

21. The method of claim 19, further comprising delivering the drugs or other agents proximate the wall of the lumen.

22. The method of claim 19, further comprising delivering the drugs or other agents to a region between the longitudinal ribs.

23. The method of 19, further comprising delivering the drugs or other agents to a region within the longitudinal ribs.

24. The method of claim 19, wherein the longitudinal ribs are compressed by a sleeve and the releasing step comprises retracting the sleeve.

25. The method of claim 19, wherein different drugs or other agents are delivered through different longitudinal ribs.

26. A method of filtering thrombolytic material from a vessel within the cardiovascular system comprising:

advancing a catheter to a desired site within the vessel;

retracting a portion of the catheter to allow a plurality of compressed longitudinal ribs in the distal portion of the catheter to flare beyond the diameter of the catheter to contact the lumen; and delivering drugs or other agents out of the catheter through the ribs.

27. The method of claim 26, wherein the delivering step comprises delivering a lytic agent.

28. The method of claim 25, further comprising delivering the lytic agent to the vessel.

29. The method of claim 26, further comprising delivering the lytic agent to a region between the longitudinal ribs.

30. The method of claim 26, further comprising delivering the lytic agent to a region within the longitudinal ribs.

31. The method of claim 26, wherein different drugs or other agents are delivered through different longitudinal ribs.

32. A catheter comprising:

a shaft with a proximal and distal portion, the distal portion comprising longitudinal ribs which in a first position flare beyond the diameter of the shaft;

a thread for compressing the longitudinal ribs such that when the thread is released from the longitudinal ribs, the longitudinal ribs flare to the first position; and means for delivering drugs to the longitudinal ribs.

33. A catheter comprising:

a shaft with a proximal and distal portion, the distal portion comprising logitudinal ribs which in a first position flare beyond the diameter of the shaft;

a member receiving at least the distal portion of the shaft, wherein the member and shaft can move with respect to each other such that when the member is retracted from the distal portion, the longitudinal ribs are in the first position and when the distal portion is within the member, the member compresses the longitudinal ribs into a second position; and means for delivering drugs or other agents to the longitudinal ribs.

34. The catheter of claim 33, wherein the member is a sleeve extending over the proximal and distal portions of the shaft.

35. A catheter comprising:

a shaft with a proximal and distal portion, the distal portion comprising filtration means which in a first position flares beyond the diameter of the shaft;

means for compressing the filtration means such that when the means for compressing is released from the filtration means the filtration means flares to the first position, so that the filtration means bears against walls of a lumen when released at a site; and means for delivering drugs or other agents to the filtration means.

* * * * *